United States Patent
Dalal et al.

(10) Patent No.: US 9,180,053 B2
(45) Date of Patent: Nov. 10, 2015

(54) CENTRAL VISION IMPAIRMENT COMPENSATION

(71) Applicant: Xerox Corporation, Norwalk, CT (US)

(72) Inventors: Edul N. Dalal, Webster, NY (US); Wencheng Wu, Webster, NY (US)

(73) Assignee: Xerox Corporation, Norwalk, CT (US)

( * ) Notice: Subject to any disclaimer, the term of this patent is extended or adjusted under 35 U.S.C. 154(b) by 379 days.

(21) Appl. No.: 13/752,631

(22) Filed: Jan. 29, 2013

(65) Prior Publication Data

US 2014/0210970 A1 Jul. 31, 2014

(51) Int. Cl.
*H04N 7/18* (2006.01)
*A61F 9/08* (2006.01)
*G02B 27/01* (2006.01)

(52) U.S. Cl.
CPC ............... *A61F 9/08* (2013.01); *G02B 27/017* (2013.01); *G02B 2027/011* (2013.01); *G02B 2027/014* (2013.01); *G02B 2027/0138* (2013.01); *G02B 2027/0178* (2013.01); *H04N 7/18* (2013.01)

(58) Field of Classification Search
CPC ............................... A61F 9/08; H04N 5/2628
USPC ............................................. 348/62, 63, 580
See application file for complete search history.

(56) References Cited

U.S. PATENT DOCUMENTS

| | | | |
|---|---|---|---|
| 5,026,151 A | 6/1991 | Waltuck et al. | |
| 5,067,019 A * | 11/1991 | Juday et al. | 348/580 |
| 5,737,060 A | 4/1998 | Kasha, Jr. | |
| 7,033,025 B2 | 4/2006 | Winterbotham | |
| 7,224,326 B2 | 5/2007 | Sefton | |
| 8,708,495 B2 * | 4/2014 | Kohn et al. | 351/246 |
| 2004/0143170 A1 | 7/2004 | DuRousseau | |
| 2007/0229397 A1 | 10/2007 | Sefton | |
| 2010/0164990 A1 | 7/2010 | Van Doorn | |
| 2012/0212594 A1 | 8/2012 | Barnes et al. | |
| 2012/0293548 A1 | 11/2012 | Perez et al. | |

* cited by examiner

*Primary Examiner* — Michael Lee
(74) *Attorney, Agent, or Firm* — Kermit D. Lopez; Luis M. Ortiz; Ortiz & Lopez, PLLC (57) ABSTRACT

A method, system, and processor-readable medium for non-invasive visual compensation for a person suffering from central vision impairment. Digital images of a target field of view can be obtained and processed to generate processed images thereof, wherein central regions of the digital images that normally would reach an impaired portion of a retina of the person are moved to other regions of the target field of view. The processed images can be presented to the person such that the central regions are now directed at an unimpaired peripheral portion of the retina of the person.

20 Claims, 5 Drawing Sheets

FIG. 5 form a part of the specification, further illustrate the
CENTRAL VISION IMPAIRMENT COMPENSATION

FIELD OF THE INVENTION

Embodiments are generally related to the field of central vision impairment. Embodiments also relate to devices, systems, and methods for assisting individuals suffering from central vision impairment. Embodiments additionally relate to image-processing and digital video visual aid devices.

BACKGROUND OF THE INVENTION

Central vision is essential to activities, such as reading or driving, where visual detail is of importance. Central vision impairment (CVI) is due to damage to the macula, the portion of the retina responsible for central vision, and can be due to a variety of pathological conditions, including macular degeneration, diabetic retinopathy, etc. Of these, macular degeneration (MD) is a disease of the eye, which is very common. There is no cure for MD and visual aids, such as special spectacles or implanted intraocular lenses, are often employed to assist the patient suffering from MD. There are many deficiencies with these methods. Note that although this disclosure discusses MD specifically, the various disclosed embodiments, however, can also apply to CVI in general without limitation to the cause of CVI.

Figure 1:
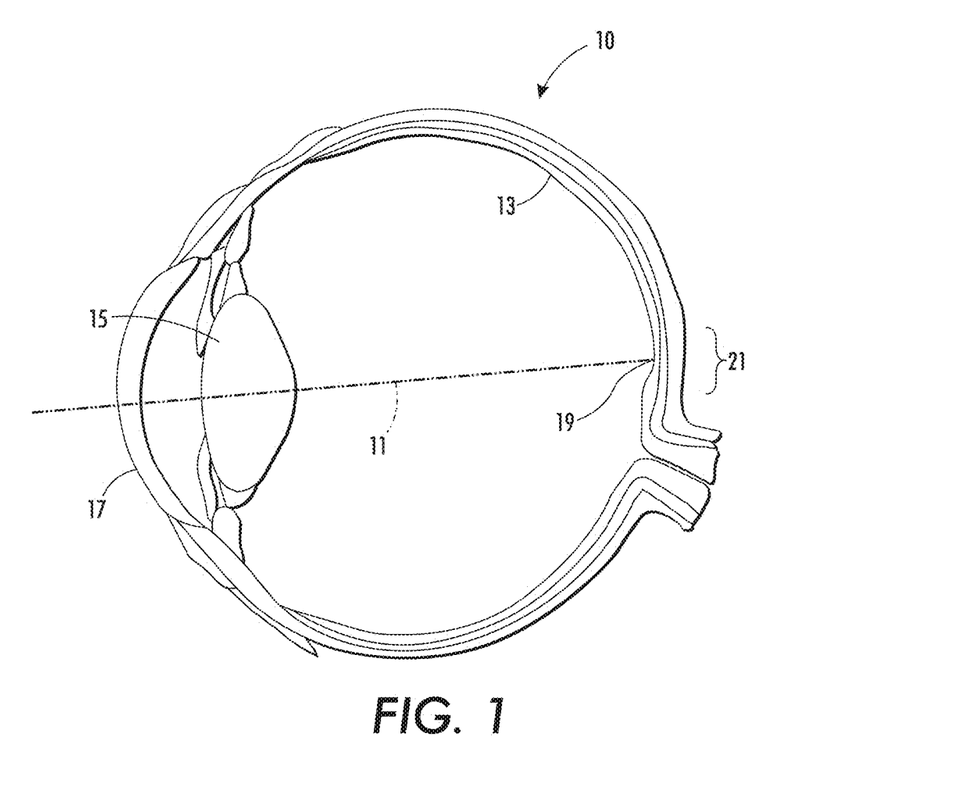
FIG. 1 illustrates a schematic diagram of the horizontal cross-section of a human eye, showing the retina and macula.

FIG. 1 illustrates a schematic diagram of the horizontal cross-section of a human eye 10, showing the retina and macula with respect to a visual axis 11. The cornea 17 and lens 15 of the eye 10 are also shown in FIG. 1, in addition to the fovea 19. In general, the retina 13, or light-sensitive region of the eye, contains the macula 21, which is the region of the retina 13 responsible for central vision. Although the macula 21 occupies less than 5% of the area of the retina 13, it is essential for any close-inspection activities such as reading. Macular degeneration (MD) is a disease of the eye (e.g., eye 10 shown in FIG. 1), which can damage part or all of the macula 21. Sufferers of macular degeneration typically retain some level of peripheral vision, so they can usually perform some normal activities such as walking. They cannot, however, perform any task requiring central vision such as reading. They are unable to use their peripheral vision for such tasks, since the obscured region of view moves with their gaze.

Figure 2A:
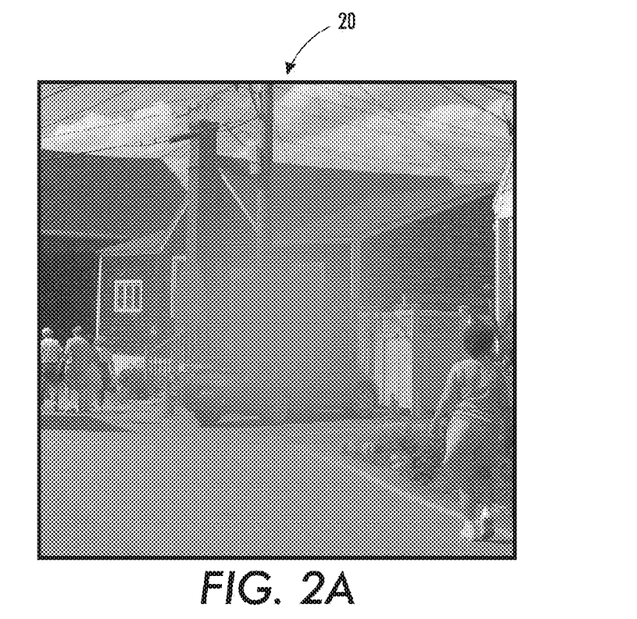
FIG. 2(a) and FIG. 2(b) illustrate simulations of the field of view of a person suffering from some forms of macular degeneration.
Figure 2B:
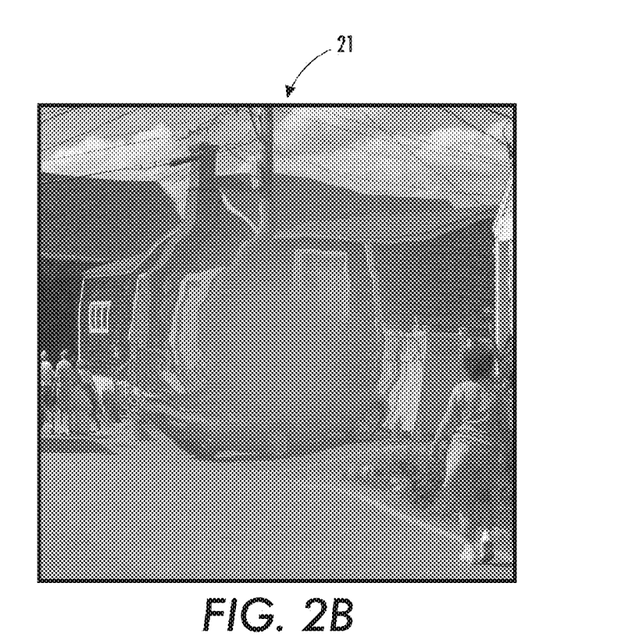
Figure 2C:
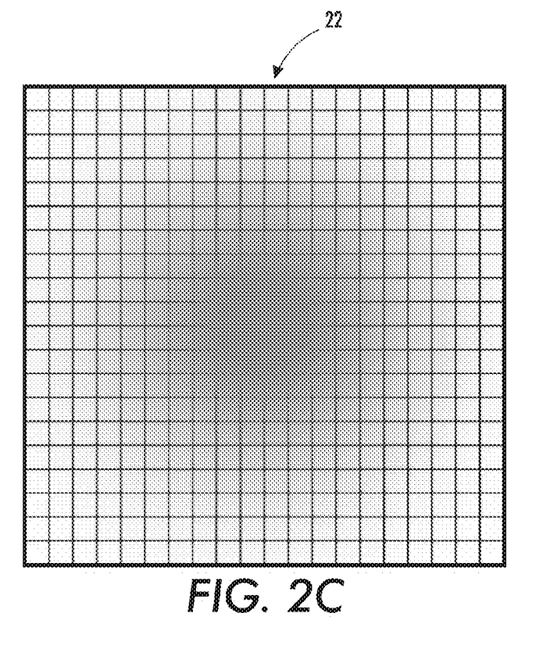
FIG. 2(c) and FIG. 2(d) illustrate simulated representations of an image deformation resulting from similar forms of MD, represented in terms of an Amsler grid test chart.
Figure 2D:
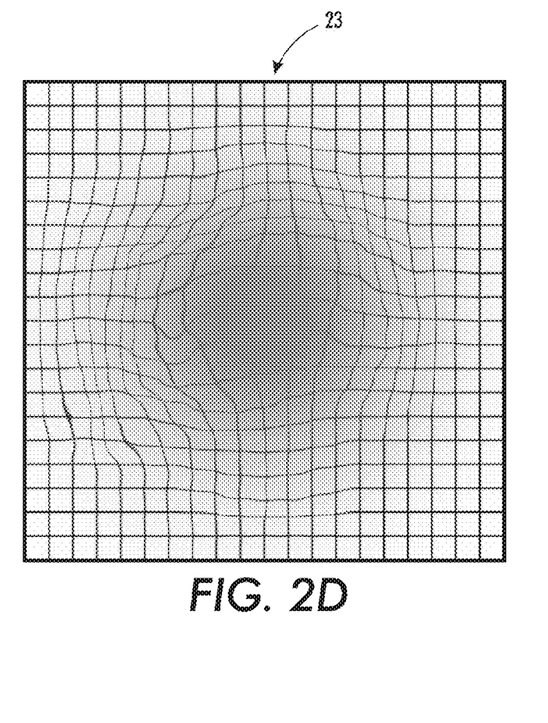

FIG. 2(a) illustrates a pictorial view of a simulation 20 of the field of view of a person suffering from some forms of macular degeneration, wherein the central vision region is obscured corresponding to the diseased portion of the retina. FIG. 2(b) illustrates a similar simulated view 21 but for a more complicated condition, wherein the central vision region is obscured as well as distorted, corresponding to the diseased portion of the retina. FIG. 2(c) and FIG. 2(d) illustrate simulated representations 22 and 23 of image deformation from similar forms of macular degeneration, represented in terms of an Amsler grid, which is commonly used in diagnosing MD. FIGS. 2(a)-2(d) thus illustrate how the sight of a person suffering from MD might be obscured and/or distorted. The obscured and/or distorted region of the image moves as the person looks at different objects, thereby always degrading the critical region of interest.

Age-related macular degeneration (AMD) is a commonly-occurring form of MD and is prevalent in older people. According to a WHO report [1], the number of visually impaired persons worldwide was 161 million, of which 8.7% (e.g., 14 million) suffered from AMD. The rate of occurrence in developed countries, with their older populations, is significantly greater, up to, for exmple, approximately 20%. Moreover, when other forms of MD and other eye diseases, which result in similar disabilities, are considered, the numbers are even greater.

Medical intervention includes pharmaceutical drugs and surgical procedures such as laser photocoagulation. Some of these have been shown to retard progression of the disease, but there is no effective cure for MD.

The primary form of treatment involves the use of vision aids which divert some of the incident light to the undiseased peripheral portion of the retina. These vision aids range from special spectacles to implantable intraocular lenses.

Special spectacles are commercially available, but they do not always work well and they can be expensive. Moreover, each pair of spectacles is typically for a specific task (e.g., reading) and unsuitable for other tasks (e.g., driving). MD is a progressive disease which gradually (or sometimes rapidly) gets worse. Such spectacles consequently need to be frequently replaced.

SUMMARY

The following summary is provided to facilitate an understanding of some of the innovative features unique to the disclosed embodiments and is not intended to be a full description. A full appreciation of the various aspects of the embodiments disclosed herein can be gained by taking the entire specification, claims, drawings, and abstract as a whole.

It is, therefore, one aspect of the disclosed embodiments to provide for methods and systems for assisting sufferers of macular degeneration.

It is another aspect of the disclosed embodiments to provide for an improved visual aid device for assisting individuals suffering from macular generation.

It is yet another aspect of the disclosed embodiments to provide for an improved image-processing method and system.

It is still another aspect of the disclosed embodiments to provide for a device for compensating for the effects of macular degeneration.

The aforementioned aspects and other objectives and advantages can now be achieved as described herein. Methods, systems, and processor-readable media are disclosed for non-invasive visual compensation for a person suffering from central vision impairment. Digital images of a target field of view can be obtained and processed to generate processed images thereof, wherein central regions of the digital images that normally would reach an impaired portion of a retina of the person are moved to other regions of the target field of view. The processed images can be presented to the person such that the central regions are now directed at an unimpaired peripheral portion of the retina of the person.

BRIEF DESCRIPTION OF THE FIGURES

The accompanying figures, in which like reference numerals refer to identical or functionally-similar elements throughout the separate views and which are incorporated in and form a part of the specification, further illustrate the present invention and, together with the detailed description of the invention, serve to explain the principles of the present invention.

DETAILED DESCRIPTION

The particular values and configurations discussed in these non-limiting examples can be varied and are cited merely to illustrate at least one embodiment and are not intended to limit the scope thereof.

The embodiments will now be described more fully hereinafter with reference to the accompanying drawings, in which illustrative embodiments of the invention are shown. The embodiments disclosed herein can be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout. As used herein, the term "and/or" includes any and all combinations of one or more of the associated listed items.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Figure 3:
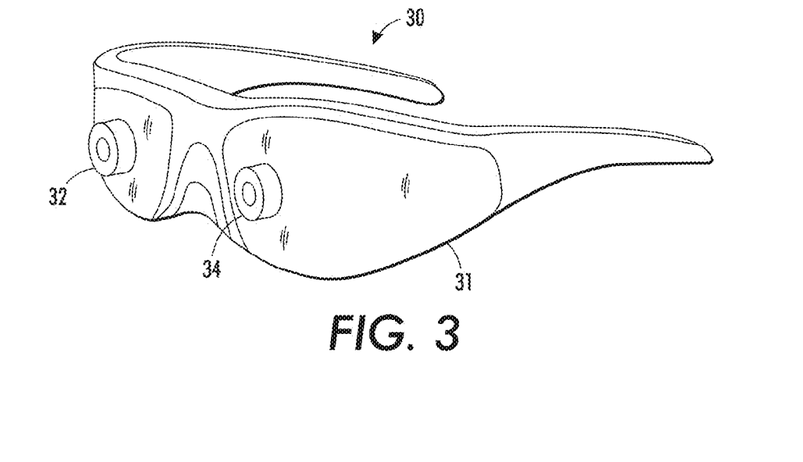
FIG. 3 illustrates a pictorial view of a system composed of a video-based device for assisting MD sufferers, in accordance with a preferred embodiment.

FIG. 3 illustrates a pictorial view of a system 30 composed of a video-based device 31 for assisting MD sufferers, in accordance with a preferred embodiment. Such a device 31 can help MD sufferers perform many normal tasks such as reading, watching TV, and driving. The mode of operation involves diverting incident light to the unimpaired peripheral portion of the retina. In some cases of MD, the impaired regions of the retina do not affect the entire macula, and/or are not centered on the macula, and in such cases, some or all of the incident light would be diverted to the unimpaired portion of the macula, instead of or in addition to the unimpaired peripheral portion of the retina. Note that hereinafter when reference is made to the "unimpaired peripheral portion of the retina," such reference also includes this expanded understanding as well.

The video-based device 31 offers a significant departure from typical physical methods (e.g., spectacles and intraocular implants) currently employed. Such a device 31 is more customizable and offers a longer useful life, in addition to being non-invasive and in many cases less expensive.

In the example embodiment illustrated in FIG. 3, the device 31 can be implemented in the context of glasses, such as Virtual Reality (VR) or Augmented Reality (AR) goggles or head-mounted displays. VR and AR are commonly used to generate "virtual or augmented environments" in which the user can be immersed. One example of an AR device, which can be adapted for use as device 31, is disclosed in U.S. Patent Application Publication No. 2012/0293548 entitled "Event Augmentation With Real-Time Information" to Perez et al., which published on Nov. 22, 2012 and which is incorporated herein by reference. Another example of an AR device or system and/or method, which can be adapted for use as device 31 is disclosed in U.S. Patent Application Publication No. 2010/0164990 entitled "System, Apparatus, and Method for Augmented Reality Glasses for End-User Programming" to Van Doorn, which published on Jul. 1, 2010 and is incorporated herein by reference.

A variety of technologies may be employed in the design of device 31. As one example, traditional liquid crystal display (LCD), liquid crystal on silicon (LCOS), ferroelectric LCD (FLC), digital light processing (DLP), light-emitting diode (LED), organic light-emitting diode (OLED) or plasma displays may be used, modified for this application. Such modification may include smaller size and higher resolution than traditional displays, due to their location close to the user's eyes in the goggles or head-mounted displays. As another example, a projection system may be used, wherein images are projected onto miniature screens or prisms from one or more digital projectors. The miniature screens are located in proximity to the user's eyes and may be planar or non-planar. As a third example, a retina scanning system may be used, wherein a laser beam is scanned directly onto the user's retina.

One or more video cameras 32, 34 (e.g., typically two, one at the center of each eye) can feed a video stream to the glasses or goggles 30. Cameras with performance similar to inexpensive web-cams, for example, may be suitable for this purpose. Video from the cameras 32, 34 can first be modified such that image content in the central vision area is mapped to the peripheral vision area, i.e., the outer regions of the field of view. Note that the generalization described earlier with respect to the "unimpaired peripheral portion of the retina" applies here and elsewhere.

Figure 4:
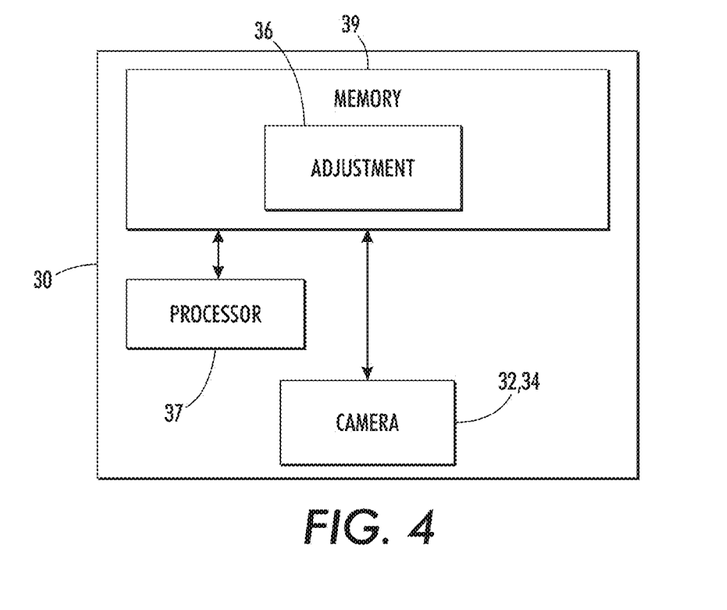
FIG. 4 illustrates a block diagram of the system shown in FIG. 3, in accordance with an alternative embodiment.

FIG. 4 illustrates a block diagram of the system 30 shown in FIG. 3, in accordance with an alternative embodiment. System 30 shown in FIG. 3 can provide for optional enhancements, which would normally be difficult or impossible to achieve with spectacles or intraocular lens implants. System 30 includes an adjustment module 36, which permits the central vision region of an image to be mapped to the peripheral vision area and adjusted to exactly match the size and shape of the defect in the user's vision, thereby using as much as possible of the unimpaired macula or peripheral retina. Here the mapping is a pre-determined spatial transformation, which allows the adjustment module 36 to convert input digital images to modified output digital images that are more suitable for MD sufferers.

A single system 30 can thus be employed for all tasks (e.g., reading, watching TV, and driving). This can be achieved by focusing the camera lens and/or adjusting the image (e.g., as described below). Note that the module 36 can in some embodiments be stored in a memory 39 and instructions provided by such modules processed via a processor 37. Note that the various components such as processor 37, memory 39, camera 32, 34 can in some embodiments, communicate with one another via a system bus represented by the double arrows shown in FIG. 4.

It can be appreciated that the modified image will not look quite like it would to one with normal vision, but the human brain is capable of handling that with some training, as is evidenced by the utility of current visual aids. Such human processing is not possible without image modification to redirect light to the peripheral retina since the critical central part of the image would be completely missing. The modified image contains all or most of the critical central part of the image, except that it is moved to the peripheral area, which is still functional in the user's retina.

Examples of the mappings used in adjustment module 36 include look-up tables, a parameterized radial expansion function, etc. These mappings can be determined via various approaches such as conducting a specially designed vision test, or conducting an instrumented physical or psychophysical measurement of the eyes of the person. For example, a person may be asked to view an Amsler grid test chart and describe the distortion seen, e.g., as shown in FIG. 2(*d*).

Alternatively, a computer-aided system consisting of a computer, a display, and a chin-rest can be used to conduct the above-mentioned vision test. For example, the exact location of the central region of a person suffering with MD can be determined by displaying dots of controlled brightness at various locations in the person's field of view and asking the person to indicate whether the dots are seen or not. Moreover, such measurements can also be made using Scanning Laser Ophthalmoscopy, wherein the dots are directly imaged on the retina of the person. By combining this with retinal imaging and an eye-tracking system, the dots can be stabilized on desired locations of the retina to compensate for eye movements during measurement.

For another example, the distortion as shown in FIG. 2(*d*) can be measured by providing a graphical user interface to allow the person to manipulate the displayed digital test chart until the distortions seen by him/her are minimized. The mapping used in the adjustment module can also be tuned to each individual task (e.g., reading versus watching TV versus driving) for each individual via a simple calibration or set-up procedure as discussed above with task-appropriate vision tests. This is readily achievable via changes in the image-processing parameters and/or methods used in the adjustment modules (e.g., use of different mappings).

Figure 5:
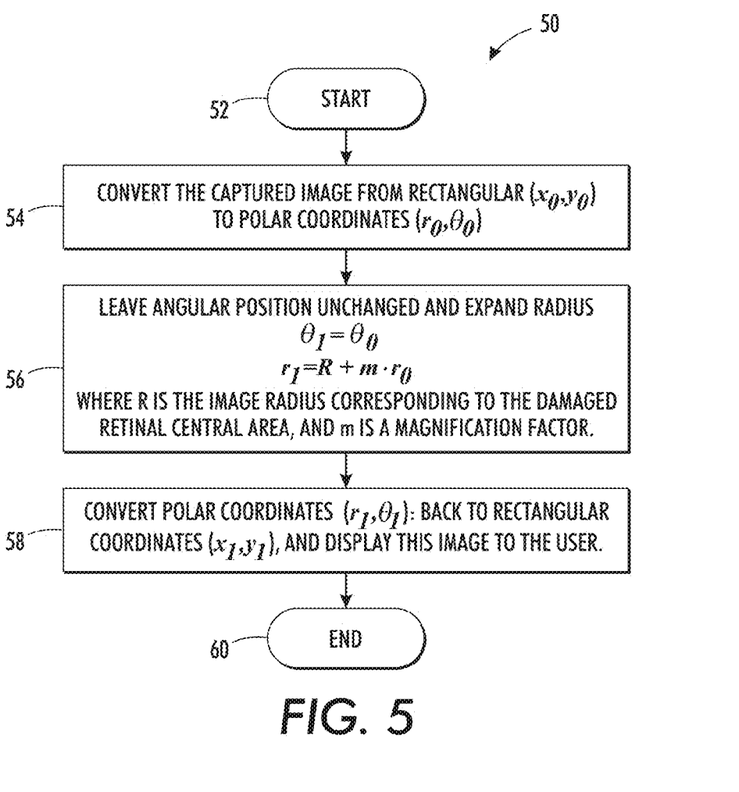
FIG. 5 illustrates a flow-chart of operations depicting an image-processing method, which can be implemented in accordance with the disclosed embodiments.

FIG. 5 illustrates a flow-chart of operations depicting an exemplary image-processing method 50, which can be implemented in accordance with the disclosed embodiments. In its simplest form, the image-processing method 50 can expand outward the central vision region corresponding to the damaged retinal area so that it is now in the peripheral vision area. Thus, the method 50 can convert real-world (camera) coordinates $(x_0, y_0)$ to modified (display) coordinates $(x_1, y_1)$. As shown at block 52, the process is initiated. Then, as depicted at block 54, a step or logical operation can be implemented to convert the captured image from rectangular $(x_0, y_0)$ to polar coordinates $(r_0, \theta_0)$. Thereafter, as illustrated at block 56, the angular position is left unchanged and the radius expanded according to:

$$\theta_1 = \theta_0$$

$$r_1 = R + m \cdot r_o$$

where the variable R represents the image radius corresponding to the damaged retinal central area and m is a magnification factor. Next, as depicted at block 58, a step or logical operation can be implemented to convert polar coordinates $(r_1, \theta_1)$ back to rectangular coordinates $(x_1, y_1)$ and display this image to the user of, for example, the goggles 31 shown in FIG. 3. Optionally, a translation $(\Delta x, \Delta y)$ may be applied before converting to polar coordinates and/or after converting back to rectangular coordinates to allow for greater flexibility in handling cases where the impaired region is not centered on the fovea.

The image radius R and magnification factor m, as well as the translation $\Delta x, \Delta y$, are adjustable parameters. The image radius R would typically be set corresponding to the damaged retinal area. It may need to be adjusted periodically (e.g., monthly or annually) if the macular damage is progressive. This adjustment can be readily done by software, either by a technician or by the user herself. The magnification factor m may be adjusted according to the task. A magnification factor of m=1 would simply push the damaged area image region out into the peripheral area. For close tasks such as reading, higher values of m may be used for better resolution, while for other tasks such as driving, lower values of m may be used to get a larger field of view. In practice, the parameters (R, m, $\Delta x$, $\Delta y$) can be selected based on a series of simple calibration or set-up procedures as discussed earlier. For example, a series of vision tests (e.g., reading some text or viewing an Amsler grid test chart at appropriate distances) can be conducted to select appropriate parameters that meet the functional requirements of the task as well as the comfort of the individual. These set-up procedures may be implemented in a computer-aided manner such that individual users can perform the adjustment on their own.

In practice, more complex algorithms may be used, e.g., to handle non-circular irregular-shaped central image region, to exactly match the damaged retinal area, so as to maximize use of the functioning part of the retina. Also, image distortions in the functioning part of the retina can be corrected by distorting the image in the inverse direction. Such complex adjustments may be conducted by using more elaborate algorithms with a greater number of parameters. Alternatively, a look-up table (LUT) may be used. Typically, simpler geometric algorithms may be adequate to correct for the primarily obscuring degradations such as shown in FIG. 2(*a*) and FIG. 2(*c*), whereas look-up tables may often be required for more complex degradations, especially those involving distortion in addition to obscuration, such as shown in FIG. 2(*b*) and FIG. 2(*d*). One example approach for achieving this is to have each user perform certain tasks based on a pre-defined set of test patterns and then use the results to derive an appropriate set of parameters for the image warping algorithms for each individual and task.

As will be appreciated by one skilled in the art, the disclosed embodiments can be implemented in the context of one or more devices and may include, for example, software (e.g., software modules) for carrying out particular instructions (e.g., to instruct a device to function in a particular manner). Accordingly, the embodiments may take the form of an entire hardware implementation (e.g., a hardware system/apparatus), an entire software embodiment or an embodiment combining software and hardware aspects.

The program code may execute entirely on, for example, device 31 and/or system 30, and/or partly on another computer, as a stand-alone software package, partly on the user's computer and partly on a remote computer or entirely via a remote computer or computing device. In the latter scenario, the remote computer may be connected to a user's computer through a local area network (LAN) or a wide area network (WAN), wireless data network e.g., WiFi, WiMax, 802.11x, and cellular network or the connection can be made to an external computer via most third party supported networks (e.g., through the Internet via an internet service provider).

The embodiments are described at least in part herein with reference to flowchart illustrations and/or block diagrams of methods, systems, and computer program products and data structures according to embodiments of the invention. It will be understood that each block of the illustrations, and combinations of blocks, can be implemented not only by hardware devices/systems, but also with the assistance of computer program instructions. These computer program instructions may be provided to a processor of a general-purpose computer, special purpose computer, or other programmable data-processing apparatus to produce a machine such that the instructions, which execute via the processor of the computer or other programmable data-processing apparatus, create means for implementing the functions/acts specified with respect to, for example, the various instructions of the process/flow or method described above.

These computer program instructions may also be stored in a computer-readable memory that can direct a computer or other programmable data-processing apparatus to function in a particular manner such that the instructions stored in the computer-readable memory produce an article of manufacture including instruction means which implement the function/act specified in, for example, a block or blocks of a process flow diagram or flow chart of logical operations (e.g., FIG. 5)

The computer program instructions may also be loaded onto a computer or other programmable data-processing apparatus to cause a series of operational steps to be performed on the computer or other programmable apparatus to produce a computer implemented process such that the instructions which execute on the computer or other programmable apparatus provide steps for implementing the functions/acts specified in the block or blocks such as the logical instructions of method 50 shown in FIG. 5.

Based on the foregoing, it can be appreciated that a number of embodiments, preferred and alternative, are disclosed herein. For example, in one embodiment, a method for non-invasive visual compensation for a person suffering from central vision impairment can be implemented. Such a method can include the steps or logical operations of, for example, obtaining digital images of a target field of view; processing the digital images to generate processed images thereof, wherein central regions of the digital images that normally would reach an impaired portion of a retina of the person are moved to other regions of the target field of view; and presenting the processed images to the person such that the central regions are now directed at an unimpaired peripheral portion of the retina of the person.

In another embodiment, the digital images can be obtained via one or more video cameras and the processed images can be presented via one or more video displays. In yet another embodiment, the video camera(s) and the video display(s) can be mounted in a configuration to follow the direction of view of the person. In still another embodiment, the video display(s) can be positioned so as to enable the output to reach a substantial portion of the unimpaired peripheral portion of the retina.

In other embodiments, the step or logical operation of processing of the images can include warping the images based on a pre-determined spatial transformation. In yet other embodiments, the pre-determined spatial transformation can include distorting the digital images such that the central region is moved radially outward and the distortion function is parameterized by a size and a location of the center of the central region to be moved and a magnification desired for moving the digital images of the central region to other regions. In still other embodiments, the pre-determined spatial transformation can include a look-up table.

In another embodiment, the pre-determined spatial transformation can be determined based on results of a set of procedures including one or more of the following: conducting a specially designed vision test and conducting an instrumented physical or psychophysical measurement of the eyes of the person.

In another embodiment, a system for non-invasive visual compensation for a person suffering from central vision impairment can be implemented. Such a system can include, for example, one or more video cameras, one or more video displays, and a processor that communicates with the video camera(s) and the video display(s). Such a system can be configured to further include a data bus coupled to the processor and a computer-usable medium embodying computer program code, the computer-usable medium being coupled to the data bus, the computer program code comprising instructions executable by the processor and configured for obtaining digital images of a target field of view, utilizing the video camera(s); processing the digital images to generate processed images thereof, wherein central regions of the digital images that normally would reach an impaired portion of a retina of the person are moved to other regions of the target field of view; and presenting the processed images to the person, utilizing the video display(s), such that the central regions are now directed at an unimpaired peripheral portion of the retina of the person.

In some system embodiments, the video camera(s) and the video display(s) can be mounted in a configuration to follow a direction of view of the person. In other system embodiments, the video display(s) can be positioned so as to enable the output to reach a substantial portion of the unimpaired peripheral portion of the retina. In other system embodiments, processing the digital images can further include warping the images based on a pre-determined spatial transformation.

In yet another system embodiment, the pre-determined spatial transformation can include distorting the digital images such that the central region is moved radially outward and the distortion function is parameterized by a size and a location of the center of the central region to be moved and a magnification desired for moving the digital images of the central region to other regions. In still another system embodiment, the pre-determined spatial transformation can include a look-up table.

In another system embodiment, the pre-determined spatial transformation can be determined based on results of a set of procedures including one or more of the following: conducting a specially designed vision test and conducting an instrumented physical or psychophysical measurement of the eyes of the person.

In other embodiments, the pre-determined spatial transformation can be customized to at least one of a specific person, a specific task, and/or a specific period of time. In still other embodiments, the video display(s) can include one or more of a virtual reality device, an augmented reality device, a head-mounted display, a laser scanning retinal display, and/or a digital projector display. Note that the central vision impairment can include macular degeneration.

In still another embodiment, a processor-readable medium storing code representing instructions to cause a process for non-invasive visual compensation for a person suffering from central vision impairment can be implemented. Such code can include code to, for example, obtain digital images of a target field of view; process the digital images to generate processed images thereof, wherein central regions of the digital images that normally would reach an impaired portion of a retina of the person are moved to other regions of the target field of view; and present the processed images to the person such that the central regions are now directed at an unimpaired peripheral portion of the retina of the person. Such digital images can be obtained via at least one video camera and the processed images are presented via at least one video display.

It will be appreciated that variations of the above-disclosed and other features and functions, or alternatives thereof, may be desirably combined into many other different systems or applications. Also, that various presently unforeseen or unanticipated alternatives, modifications, variations or improvements therein may be subsequently made by those skilled in the art which are also intended to be encompassed by the following claims.

What is claimed is:

1. A method for non-invasive visual compensation for a person suffering from central vision impairment, said method comprising:
   obtaining digital images of a target field of view for conversion of said digital images from rectangular coordinates $(x_0, y_0)$ to polar coordinates $(r_0, \theta_0)$;
   processing said digital images to generate processed images thereof including polar coordinates $(r_1, \theta_1)$ converted back to rectangular coordinates $(x_1, y_1)$ wherein central regions of said digital images that normally would reach an impaired portion of a retina of said person are moved to other regions of said target field of view; and
   presenting said processed images to said person such that said central regions are now directed at an unimpaired peripheral portion of said retina of said person, thereby expanding outward a central vision region corresponding to a damaged retinal area of said retina of said person so that said central vision region is now in a peripheral vision area.

2. The method of claim 1, wherein processing said digital images further includes leaving an angular position unchanged and expanding a radius according to $\theta_1 = \theta_2$ and $r_1 = R + m \cdot r_0$ wherein R represents an image radius corresponding to a damaged retinal central area of said retina of said person and m represents a magnification factor and wherein said digital images are obtained via at least one video camera and said processed images are presented via at least one video display.

3. The method of claim 2, wherein said at least one video camera and said at least one video display are mounted in a configuration to follow a direction of view of said person.

4. The method of claim 3, wherein said at least one video display is positioned so as to enable the output to reach a substantial portion of said unimpaired peripheral portion of said retina.

5. The method of claim 2, wherein said processing of said images comprises warping said images based on a pre-determined spatial transformation.

6. The method of claim 5, wherein said pre-determined spatial transformation comprises distorting said digital images such that said central region is moved radially outward and the distortion function is parameterized by a size and a location of said center of said central region to be moved and a magnification desired for moving said digital images of said central region to other regions.

7. The method of claim 5, wherein said pre-determined spatial transformation comprises a look-up table.

8. The method of claim 5, wherein said pre-determined spatial transformation is determined based on results of a set of procedures including:
   conducting a specially designed vision test; and
   conducting an instrumented physical or psychophysical measurement of the eyes of said person.

9. A system for non-invasive visual compensation for a person suffering from central vision impairment, said system comprising:
   at least one video camera;
   at least one video display;
   a processor that communicates with said at least one video camera and said at least one video display;
   a data bus coupled to said processor; and
   a computer-usable medium embodying computer program code, said computer-usable medium being coupled to said data bus, said computer program code comprising instructions executable by said processor and configured for:
      obtaining digital images of a target field of view utilizing said at least one video camera for conversion of said digital images from rectangular coordinates $(x_0, y_0)$ to polar coordinates $(r_0, \theta_0)$;
      processing said digital images to generate processed images thereof including polar coordinates $(r_1, \theta_1)$ converted back to rectangular coordinates $(x_1, y_1)$ wherein central regions of said digital images that normally would reach an impaired portion of a retina of said person are moved to other regions of said target field of view; and
      presenting said processed images to said person utilizing said at least one video display such that said central regions are now directed at an unimpaired peripheral portion of said retina of said person, thereby expanding outward a central vision region corresponding to a damaged retinal area of said retina of said person so that said central vision region is now in a peripheral vision area.

10. The system of claim 9, wherein processing said digital images further includes leaving an angular position unchanged and expanding a radius according to $\theta_1 = \theta_2$ and $r_1 = R + m \cdot r_0$ wherein R represents an image radius corresponding to a damaged retinal central area of said retina of said person and m represents a magnification factor and wherein said at least one video camera and said at least one video display are mounted in a configuration to follow a direction of view of said person.

11. The system of claim 10, wherein said at least one video display is positioned so as to enable the output to reach a substantial portion of said unimpaired peripheral portion of said retina.

12. The system of claim 10, wherein said processing said digital images further comprises warping said images based on a pre-determined spatial transformation.

13. The system of claim 12, wherein said pre-determined spatial transformation comprises distorting said digital images such that said central region is moved radially outward and the distortion function is parameterized by a size and a location of said center of said central region to be moved and a magnification desired for moving said digital images of said central region to other regions.

14. The system of claim 13, wherein said pre-determined spatial transformation comprises a look-up table.

15. The system of claim 13, wherein said pre-determined spatial transformation is determined based on results of a set of procedures including at least one of:
   conducting a specially designed vision test; and
   conducting an instrumented physical or psychophysical measurement of the eyes of said person.

16. The system of claim 13, wherein said pre-determined spatial transformation is customized to:
   a specific person;
   a specific task; and a specific period of time.

17. The system of claim 10, wherein said at least one video display comprises at least one of:
- a virtual reality device;
- an augmented reality device;
- a head-mounted display;
- a laser scanning retinal display, and
- a digital projector display.

18. The system of claim 10, wherein said central vision impairment comprises macular degeneration.

19. A processor-readable medium storing code representing instructions to cause a process for non-invasive visual compensation for a person suffering from central vision impairment, said code comprising code to:
- obtain digital images of a target field of view for conversion of said digital images from rectangular coordinates ($x_0, y_0$) to polar coordinates ($r_0, \theta_0$);
- process said digital images to generate processed images thereof including polar coordinates ($r_1, \theta_1$) converted back to rectangular coordinates ($x_1, y_1$), wherein central regions of said digital images that normally would reach an impaired portion of a retina of said person are moved to other regions of said target field of view; and
- present said processed images to said person such that said central regions are now directed at an unimpaired peripheral portion of said retina of said person, thereby expanding outward a central vision region corresponding to a damaged retinal area of said retina of said person so that said central vision region is now in a peripheral vision area.

20. The processor-readable medium of claim 19, wherein processing said digital images further includes leaving an angular position unchanged and expanding a radius according to $\theta_1 = \theta_2$ and $r_1 = R + m \cdot r_0$ wherein R represents an image radius corresponding to a damaged retinal central area of said retina of said person and m represents a magnification factor and wherein said digital images are obtained via at least one video camera and said processed images are presented via at least one video display.

* * * * *